(12) United States Patent
Kishi et al.

(10) Patent No.: US 8,009,140 B2
(45) Date of Patent: Aug. 30, 2011

(54) MASTER-SLAVE MANIPULATOR SYSTEM

(75) Inventors: Kosuke Kishi, Mito (JP); Makoto Hashizume, Kasuga (JP)

(73) Assignees: Hitachi, Ltd., Tokyo (JP); Kyushu University, Fukuoka (JP)

( * ) Notice: Subject to any disclaimer, the term of this patent is extended or adjusted under 35 U.S.C. 154(b) by 838 days.

(21) Appl. No.: 12/016,231

(22) Filed: Jan. 18, 2008

(65) Prior Publication Data

US 2008/0180392 A1    Jul. 31, 2008

(30) Foreign Application Priority Data

Jan. 19, 2007    (JP) ................................. 2007-009922

(51) Int. Cl.
G09G 5/00    (2006.01)
(52) U.S. Cl. .......... 345/156; 345/157; 345/158; 345/161
(58) Field of Classification Search .......... 345/156–168, 345/204–215
See application file for complete search history.

(56) References Cited

U.S. PATENT DOCUMENTS

| | | | |
|---|---|---|---|
| 5,876,325 | A | 3/1999 | Mizuno et al. |
| 6,246,200 | B1 | 6/2001 | Blumenkranz et al. |
| 7,391,177 | B2 * | 6/2008 | Kishi et al. ................ 318/567 |
| 2003/0228039 | A1 | 12/2003 | Green | |

FOREIGN PATENT DOCUMENTS

| | | |
|---|---|---|
| EP | 1 724 071 | 11/2006 |
| JP | 7-90492 | 10/1995 |
| JP | 3583777 | 8/2004 |
| JP | 2005-103741 | 4/2005 |
| JP | 2006-321027 | 11/2006 |
| WO | WO 93/13916 | 7/1993 |
| WO | WO 00/60521 | 10/2000 |

OTHER PUBLICATIONS

Extended European Search Report issued in European Patent Application No. 08000858.4 on Feb. 7, 2011.
Office Action issued in Japanese Patent Application No. 2007-009922 on Mar. 8, 2011.

* cited by examiner

Primary Examiner — Vijay Shankar
(74) Attorney, Agent, or Firm — Antonelli, Terry, Stout & Kraus, LLP.

(57) ABSTRACT

In a master-slave manipulator system, an intuitive operation can be achieved by a simple structure in which a layout of a monitor and an operation input device is not limited. A master-slave manipulator system is provided with a manipulator, a camera, a monitor, an operation input device, a manipulator controller and a master controller. The master controller is provided with an operation an information acquisition portion for operation command acquiring an operation reference data on the basis of the command by the operation input device, an acquirement information division portion dividing the operation reference data into a position movement reference data and an orientation reference data, and a moving direction compensation controller compensating the position movement reference data on the basis of the orientation reference data so as to output a position moving command compensation information. The manipulator controller controls the position and orientation of the manipulator on the basis of the position moving command compensation information and the orientation reference data.

14 Claims, 5 Drawing Sheets

MASTER-SLAVE MANIPULATOR SYSTEM

BACKGROUND OF THE INVENTION (1) Field of the Invention

The present invention relates to a master-slave manipulator system.

(2) Description of Related Art

There have been developed a lot of master-slave manipulator systems structured such that an operator operates an operation input device, and a manipulator operates in accordance with the operation.

As a conventional master-slave manipulator system, there can be listed up JP-B2-7-90492 (patent document 1), JP-B2-3583777 (patent document 2), WO/00/60521 (patent document 3) and the like.

The patent document 1 is structured such as to detect a direction of an optical axis of a camera, and always bring a traveling direction of a manipulator main body within a screen into line with an operating direction of the operation input device regardless of a movement of a view point in accordance with a visual sense coordinate transformation.

Further, the patent document 2 is structured such as to contrive a positional relation among a manipulator, a camera, a monitor, an operator and an operation input device so as to make coordinate systems substantially the same.

Further, the patent document 3 defines positions of a monitor and an operation input device, and achieves a master-slave operation control on the basis of a camera coordinate.

In the master-slave manipulator system, in general, the operator frequently operates the operation input device from a position which is away from the manipulator so as to move the manipulator. Accordingly, the operator can operate while viewing the image of the manipulator imaged by the camera on the monitor. In this case, in a relevant coordinate system, there are mixed several coordinate systems such as a coordinate system of the manipulator, a coordinate system of the camera, a coordinate system on the monitor, a coordinate system of the operation input device, a coordinate system of the operator and the like.

Accordingly, it is necessary to understand a relation between the coordinate systems and be accustomed to an operating method at a time when the operator carries out the operation, and the operation is hard to be said as an intuitive operation. Particularly, in the case of carrying out a command about an orientation by the operation input device as well as commanding a position of a leading end of the manipulator, a lot of degrees of freedom are operated, and there is a problem that the operator is hard to operate.

Further, in the case of operating from a state in which an orientation of an end point portion of the manipulator is different from an orientation of the operation input device, the operator is hard to understand a correspondence of the commanding direction of the position and the orientation and a long time is necessary for being accustomed thereto.

On the contrary, there can be considered to control such that the orientation of the end point portion of the manipulator always comes into line with the orientation of the operation input device by installing an actuator in the operation input device. However, in this method, there is a case that such a position and orientation that the manipulator is easily actuated, however, a wrist of the operator operating the operation input device is hard to work is generated. Further, in the case that one operator operates a plurality of manipulators, it is necessary to prepare a plurality of operation input devices which correspond to all the orientations of a plurality of manipulators, so that there is generated a problem that the apparatus is enlarged in size and the operation is hard to be carried out. Accordingly, there has been known that it is necessary to provide a method capable of intuitively carrying out the operation even if the orientation of the manipulator is different from the orientation of the operation input device.

These problems remarkably appear particularly at a time of using a camera and a monitor capable of achieving a three-dimensional stereoscopic vision. The stereoscopic vision monitor displays a working area and the manipulator in a three-dimensional manner, however, in the case that the three-dimensional display is offset from a real thing in the position and orientation, there is a case that a disturbance is applied to the operator. On the contrary, these problems can be solved by defining an installed orientation of the stereoscopic vision monitor in such a manner as to be displayed by the same orientation as the actual working area or arranging the operation input device behind the stereoscopic vision monitor, in accordance with a method of bringing an orientation of an operation input device operation interface into line with an orientation of the end effector reflected on the stereoscopic vision monitor. However, the positions and orientations of the monitor and the operation input device are defined, and it is hard to freely arrange and downsize.

In this case, the patent document 1 is structured such that the moving direction within the monitor screen comes into line with the moving direction of the operation input device with regard to the command of the position, however, the orientation of the manipulator end point has not been considered. Further, in the patent document 2 and the patent document 3, the layout of the monitor and the operation input device is limited, and it is hard to freely arrange.

BRIEF SUMMARY OF THE INVENTION

An object of the present invention is to provide a master-slave manipulator system which can carry out an intuitive operation by a simple structure in which a layout of a monitor and an operation input device is not limited.

In order to achieve the object mentioned above, in accordance with present invention, there is provided a master-slave manipulator system comprising:

a manipulator having an end effector;

a camera imaging the manipulator and a working area of the manipulator;

a monitor displaying an image which the camera images so as to provide;

an operation input device outputting a command for operating the manipulator;

a master controller generating and outputting a control reference data on the basis of the command of the operation input device; and a manipulator controller controlling a position and orientation of the manipulator on the basis of the control reference data output from the master controller, wherein the master controller comprises:

an information acquisition portion for operation command acquiring an operation reference data on the basis of the command by the operation input device;

an acquirement information division portion dividing the operation reference data into a position movement reference data and an orientation reference data; and a moving direction compensation controller compensating the position movement reference data on the basis of the orientation reference data so as to output a position moving command compensation information, and wherein the manipulator controller is structured such as to control the position and orientation of the manipulator on the basis of the position moving command compensation information and the orientation reference data.

Preferable structures in accordance with the present invention will be exemplified as follows.

(1) The end effector is structured such as to have the position and orientation having six degrees of freedom, the information acquisition portion for operation command is structured such as to acquire an operation reference data having six degrees of freedom on the basis of the command by the operation input device, and the acquirement information division portion is structured such as to divide the operation reference data into a position movement reference data having three degrees of freedom and an orientation reference data having three degrees of freedom.

(2) The orientation of the end effector is calculated hour by hour, and the position movement reference data is corrected on the basis of the orientation of the end effector calculated hour by hour.

(3) The operation input device is provided with an input device gripping portion in a leading end portion, and the moving direction compensation controller is structured such as to calculate the orientation of the input device gripping portion hour by hour, calculate a moving amount and a changed orientation of the operation input device on the basis of the orientation of the input device gripping portion calculated hour by hour, and calculate a coordinate of the end effector hour by hour by using the calculated moving amount and changed orientation of the operation input device.

(4) The operation input device is provided with a moving mechanism having three direct acting joints and three rotating joints and a sensor such as an encoder, a potentiometer or the like capable of acquiring each of joint values, and the information acquisition portion for operation command is structured such as to acquire the operation reference data having six degrees of freedom on the basis of an electric signal of the position and orientation acquired by the sensor.

(5) The operation input device is provided with an input device gripping portion for manually operating the moving mechanism in a leading end portion of the moving mechanism, and the information acquisition portion for operation command is structured such as to acquire the position and orientation of the input device gripping portion on the basis of an electric signal acquired by the sensor.

(6) A plurality of the manipulators are installed, and the operation input device is constituted by a double arm type operation input device.

(7) The end effector is constituted by an operation tool, the camera is constituted by a three-dimensional endoscope, and the input device gripping portion has a grip opening and closing mechanism for opening and closing the operation tool.

In accordance with the master-slave manipulator system of the present invention, the intuitive operation can be achieved by a simple structure having no limit in the layout of the monitor and the operation input device.

Other objects, features and advantages of the invention will become apparent from the following description of the embodiments of the invention taken in conjunction with the accompanying drawings.

DETAILED DESCRIPTION OF THE INVENTION

A description will be given below of a master-slave manipulator system in accordance with an embodiment of the present invention with reference to FIGS. 1 to 5.

Figure 1:
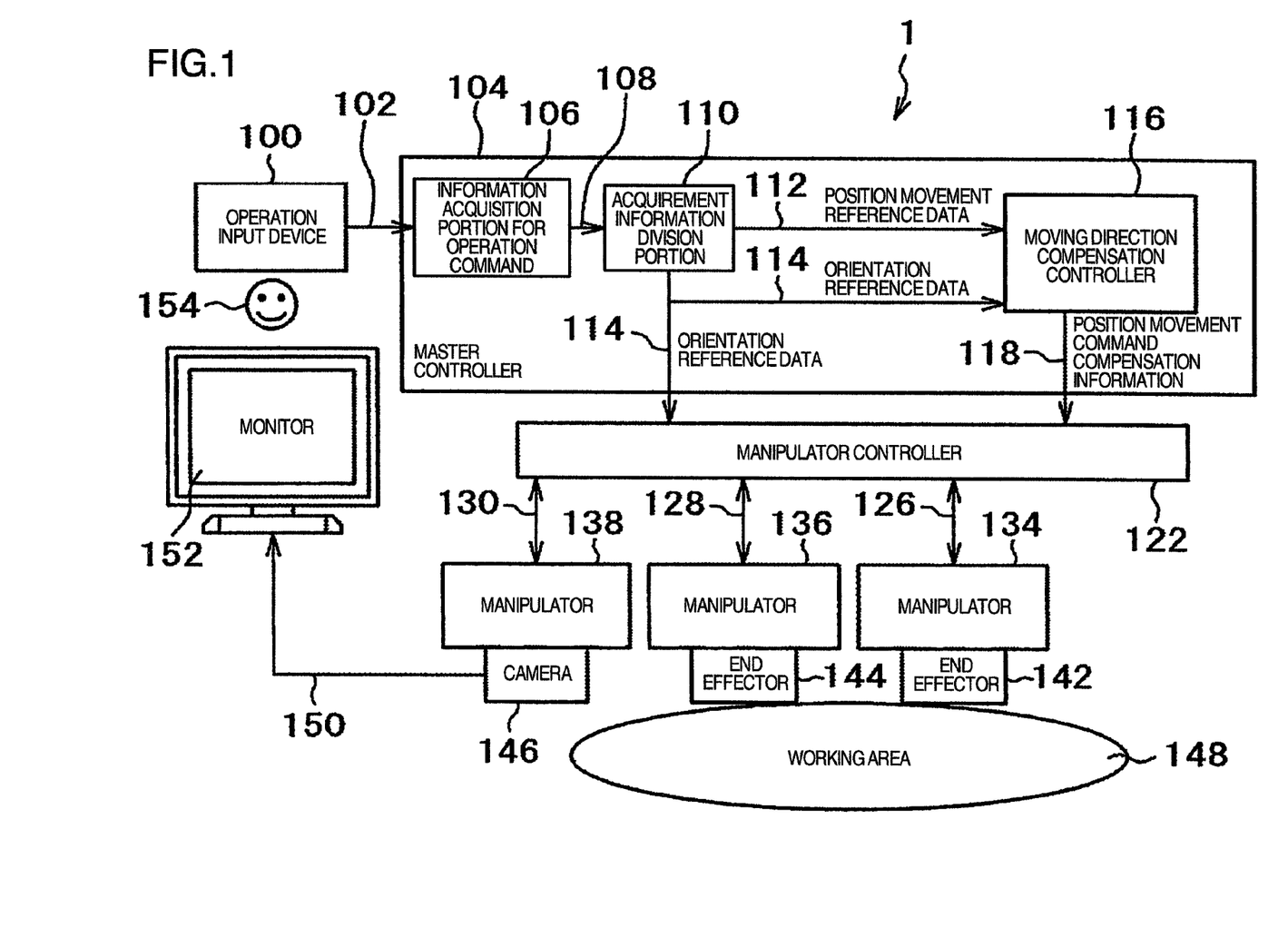
FIG. 1 is a schematic view of a whole structure of a master-slave manipulator system in accordance with an embodiment of the present invention.

First, a description will be given of a whole of a master-slave manipulator system 1 in accordance with the present embodiment with reference to FIG. 1. FIG. 1 is a schematic view of a whole structure of the master-slave manipulator system 1 in accordance with an embodiment of the present invention. The master-slave manipulator system 1 in accordance with the present embodiment constructs an operation backup master-slave manipulator system.

The master-slave manipulator system 1 is provided with manipulators 134, 136 and 138, a camera 146, a monitor 152, an operation input device 100, a manipulator controller 122, and a master controller 104.

The manipulator 134 and 136 are structured such that end effectors 142 and 144 have positions and orientations having six degrees of freedom, and are installed at plural numbers (two in an illustrated embodiment). The end effectors 142 and 144 are constructed by an operation tool used by being inserted to a body cavity. The manipulator 138 is structured such that the retained camera 146 has six degrees of freedom. The camera 146 is structured movable by the manipulator 138 in such a manner as to image the manipulators 134 and 136 and a working area 148. The camera 146 is constituted by a three-dimensional endoscope, and the work subject portion 148 is constituted by an affected part. The monitor 152 corresponds to a display portion displaying an image imaged and provided by the camera 146 on a screen.

The operation input device 100 corresponds to an input device for giving instructions for operating the manipulators 134, 136 and 138. The master controller 104 corresponds to a controller generating a control reference data on the basis of the instruction by the operation input device 100 so as to output to the manipulator controller 122. The manipulator controller 122 corresponds to a controller controlling the positions and orientations of the manipulators 134, 136 and 138 on the basis of the control reference data of the master controller 104.

Further, the master controller 104 is provided with an information acquisition portion for operation command 106, an acquirement information division portion 110, and a moving direction compensation controller 116. The information acquisition portion for operation command 106 corresponds to an acquirement portion for acquiring an operation reference data having six degrees of freedom on the basis of the command by the operation input device 100. The acquirement information division portion 110 corresponds to a dividing portion for dividing the operation reference data into a position movement reference data having three degrees of freedom and an orientation reference data having three degrees of freedom. The moving direction compensation controller 116 corresponds to a compensation controller for correcting the position movement reference data on the basis of the orientation reference data so as to output a position movement command compensation information.

Further, the manipulator controller 122 is structured such as to control the positions and orientations of the manipulators 134 and 136 on the basis of the position movement command compensation information and the orientation reference data.

An operator 154 carries out some kind or another work with respect to the work subject portion 148 by operating the operation input device 100 so as to move the end effectors 142 and 144 while viewing the work subject portion 148 and the end effectors 142 and 144 imaged by the camera 146 on the monitor 152. In this case, in the present embodiment, the operation input device 100 is structured of a double arm type, and can operate each of two manipulators 134 and 136, however, only one operation input device 100 and only one master controller 104 are illustrated.

The position and orientation instructed by the operation input device 100 is transmitted as an encoder electric signal (not shown) of the operation input device to the information acquisition portion for operation command 106 of the master controller 104 via a communication path 102. The encoder electric signal is converted into an operation reference data having six degrees of freedom corresponding to the position and orientation information by the information acquisition portion for operation command 106, and is transmitted to the acquirement information division portion 110 through a communication path 108.

The operation reference data is divided into the information relating to the position and the information relating to the orientation in the acquirement information division portion 110. The information relating to the position is transmitted as a position movement reference data 112 having three degrees of freedom, and the information relating to the orientation is transmitted as an orientation reference data 114 having three degrees of freedom, to the moving direction compensation controller 116 from the acquirement information division portion 110.

Figure 4:
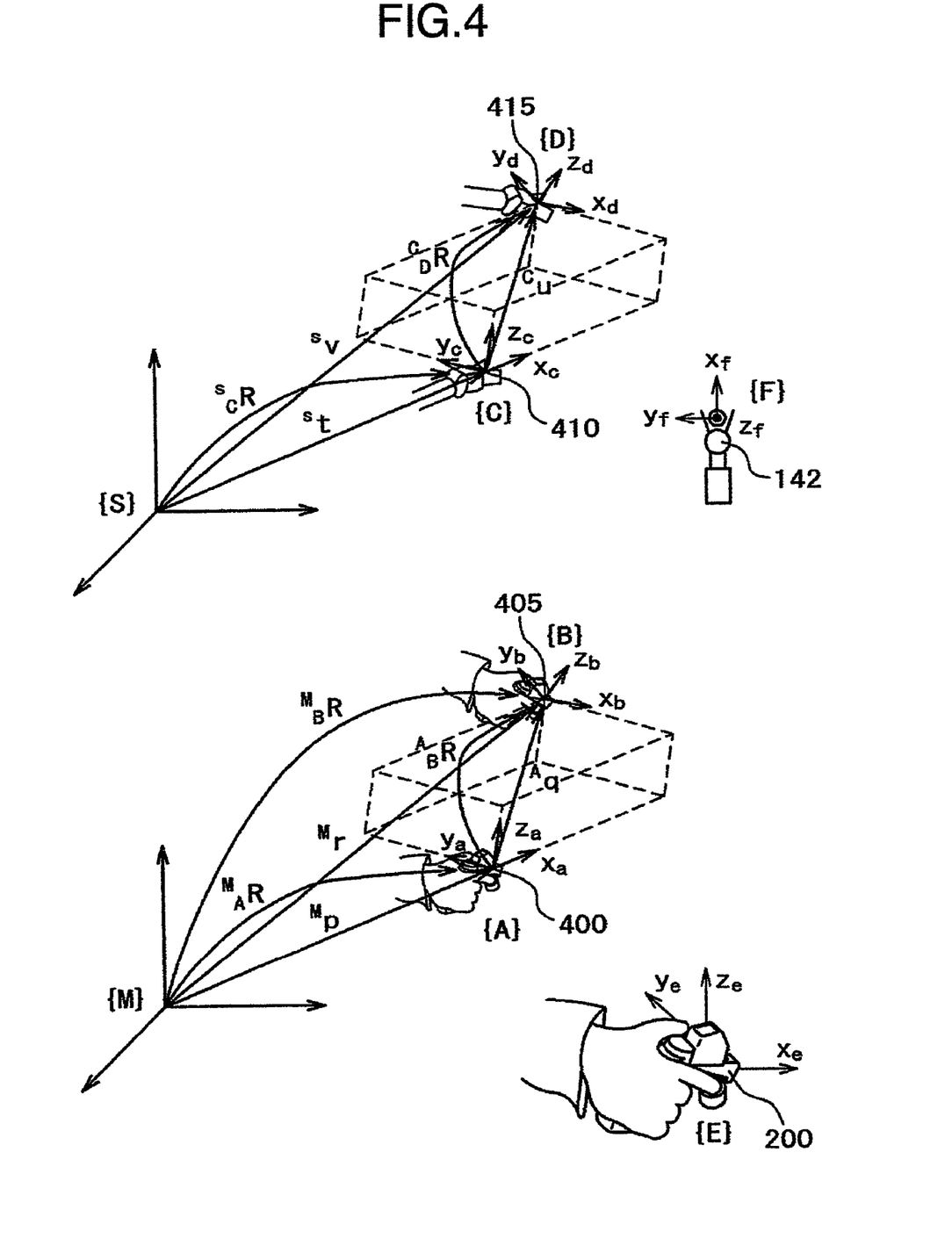
FIG. 4 is a perspective schematic view explaining a corresponding relation of movement between an input device gripping portion and an end effector in the present embodiment.

The position movement reference data 112 and the orientation reference data 114 transmitted to the moving direction compensation controller 116 are converted into a position movement command compensation information 118 by using a compensating method mentioned below with reference to FIG. 4 in the moving direction compensation controller 116, and are transmitted to the manipulator controller 122. Further, the orientation reference data output from the acquirement information division portion 110 is transmitted also to the manipulator controller 122.

The manipulator controller 122 controls in such a manner as to move the position and orientation of the end effectors 142 and 144 on the basis of the position movement command compensation information 118 and the orientation reference data 114. In this case, the camera 146 is retained by the manipulator 138, and can be operated in the same manner as the end effectors 142 and 144 by using the operation input apparatus 100, the master controller 104 and the manipulator controller 122.

Figure 2:
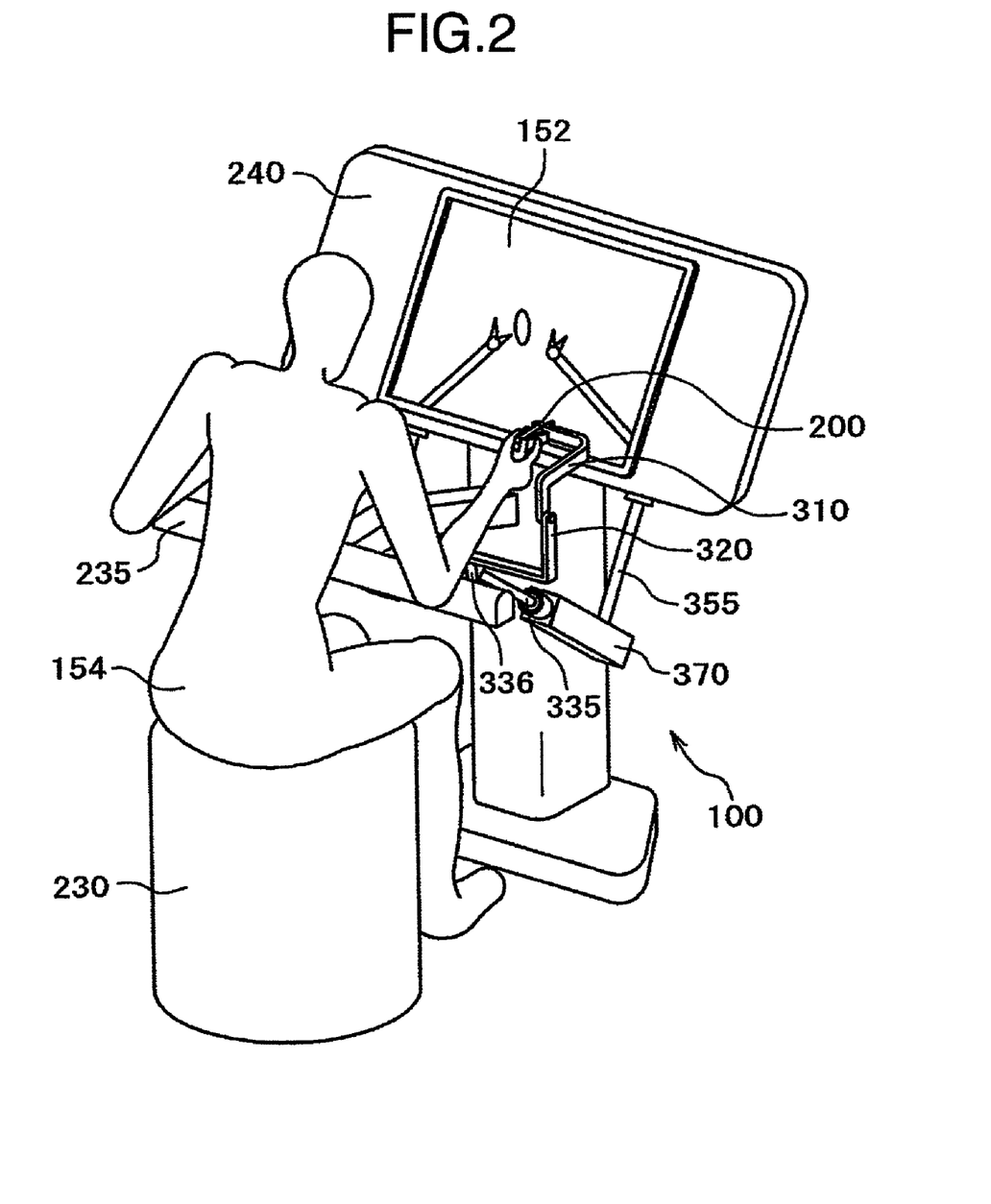
FIG. 2 is a perspective view showing a state of the present embodiment in which an operator carries out an operation of a manipulator by an operation input device.

Next, a description will be given specifically of the operation input device 100 with reference to FIG. 2. FIG. 2 is a perspective view showing a state of the present embodiment in which the operator 154 carries out the operations of the manipulators 134, 136 and 138 by the operation input device 100.

The operator 154 sits on a chair 230, puts an elbow or a front arm on an arm rest 235, and grips an input device gripping portion 200 corresponding to an input interface of the operation input device 100. The operator 154 can move the end effectors 142 and 144 displayed on the operator reference monitor 152 or the camera 146 transmitting the image to the monitor 152, by moving the input device gripping portion 200 while viewing the monitor 152. In this case, a three-dimensional stereoscopic vision monitor is preferable for the monitor 152, however, a two-dimensional monitor may be employed.

The input device gripping portion 200 is connected to an operator console 240 via a moving mechanism such as links 310, 320 and 330, a rod 335, a linear guide 370, a fixing device 355 and the like. The members are connected to each other as a rotating joint or a linear motion joint, and each of joint values can be acquired by an encoder or a potentiometer (not shown). FIG. 2 only illustrates the input device gripping portion 200 for a right arm of the operator, however, the same input interface is provided for a left arm.

In this case, the arm rest 235 is installed by extending from a center column of the operator console 240, however, is arranged in such a manner as to be prevented from physically interfering with a motion range of the operation input device 190. A switch for inputting a command to the operation input device 100, a lamp for providing the information and the like which are not illustrated, are installed on a member connecting the center column of the operator console 240 and the arm rest 235.

Figure 3:
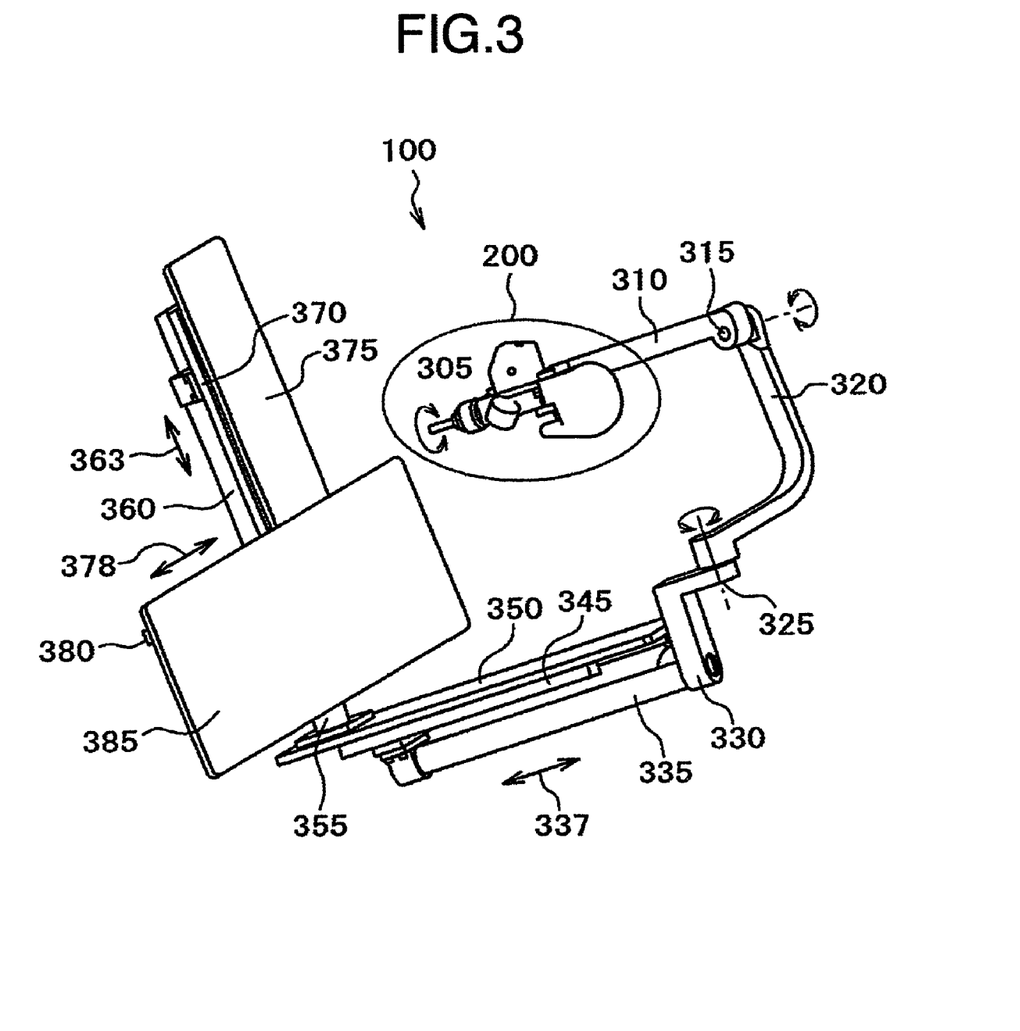
FIG. 3 is a perspective view showing a full view of one arm of a double arm type operation input device in which an operator console in the present embodiment is omitted.

Next, a description will be given further of the operation input device 100 while referring to FIG. 3. FIG. 3 is a perspective view showing a full view of one arm of the double arm type operation input device 100 in which the operator console in the present embodiment is omitted. Since the other arm is basically the same, an illustration and an overlapping description will be omitted.

A base 385 is movably attached to a back surface of the operator console 240, and a linear guide rail 380 is fixedly installed to a back surface of the base 385. The base 375 is provides in such a manner as to move in a direction (a horizontal direction) of an arrow 378 on the linear guide rail 380.

A linear guide rail 370 is installed in a fixing manner to a back surface of the base 375. The rod 360 is provided in such a manner as to linearly move in a direction (a vertical direction) of an arrow 363 on the linear guide 370 installed on the base 375. A base 350 is fixed to the rod 360 via a fixing device 355.

A rod 335 is provided with respect to the base 350 so as to linearly move in a direction (a forward and backward direction) of an arrow 337 along a linear guide 345. The fixing device 330 is attached to the rod 335. The fixing device 330 is connected to the link 320 via a shaft 325. The fixing device 330 attached to the rod 335 is connected to the link 320 via the shaft 325. The link 320 forms a rotating joint with respect to the fixing device 330 via the shaft 325. The link 320 is connected to the link 310 by using a shaft 315 as a rotating shaft. The link 310 forms a rotating joint with respect to the link 320 via the shaft 315. The link 310 is connected to the input device gripping portion 200 via a shaft 305. The input device gripping portion 200 forms a rotating joint with respect to the link 310 via the shaft 315. The input device gripping portion 200 is provided for manually operating the moving mechanism.

The operation input device 100 is structured such as to have three linear joints and three rotating joints, and the operator 154 can easily input six degrees of freedom of the position and orientation. In this case, a grip opening and closing mechanism for opening and closing the end effector 142 is attached to the input device gripping portion 200. The operation input device 100 is structured such that a motion is not transmitted to the linear motions 337, 363 and 378, only the rotating shafts 325, 315 and 305 are rotated, and the orientation reference data can be easily acquired at a time when the operator 154 moves the wrist so as to input the orientation, by contriving magnitudes of the links 310 and 320 and the input device gripping portion 200. In the same manner, the position reference data can be easily calculated only by acquiring the values of the linear motions 337, 363 and 378. In this case, a sensor such as a rotary encoder, a linear encoder or the like which is not illustrated is attached to each of the joints, and a joint value can be acquired by reading each value.

The position movement reference data 112 and the orientation reference data 114 can be easily divided in the acquirement information division portion 106 by using the operation input device 100. The position movement reference data 112 and the orientation reference data 114 may be divisionally acquired by dissolving kinematics of the operation input device.

A constant load spring (not shown) is arranged in the linear motion joint corresponding to the arrows 363 and 337 for compensating its own weight of the operation input device. Accordingly, the operator can freely operate without being sensitive about its own weight of the operation input device at a time of operating while holding the input device gripping portion 200.

Next, a description will be given of a compensating method executed by the moving direction compensation controller 116 with reference to FIG. 4. FIG. 4 is a perspective schematic view explaining a corresponding relation of movement between the input device gripping portion 200 and the end effector 142 in the present embodiment.

Thereafter, a coordinate indicating a certain rigid orientation is expressed by {coordinate system}. For example, in the case that an absolute coordinate system is set, for example, $\{O\}$, an orientation of a coordinate system $\{K\}$ as seen from $\{O\}$ is expressed by $O_K R$, and an orientation of a coordinate system $\{L\}$ as seen from $\{o\}$ is expressed by $O_L R$. In the same manner, a homogenous transformation matrix indicating the position and the orientation of the rigid body is expressed by $O_K H$, $O_L H$ or the like. Further, a vector expressed by the coordinate system $\{K\}$ is expressed by $K_p$. Further, a coordinate system $\{E\}$ based on the gripping portion is set in the input device gripping portion 200, and elementary vectors at this time are expressed by Xe, Ye and Ze. In the same manner, a coordinate system $\{F\}$ based on the end effector is set in the end effector 142, and elementary vectors at this time are expressed by Xf, Yf and Zf.

It is assumed that the input device gripping portion 200 exists in the position and orientation 400, and the end effector 142 exists in the position and orientation 410. In order to move the end effector 142 from the position and orientation 410 to the position and orientation 415, the input device gripping portion 200 is moved from the position and orientation 400 to the position and orientation 405. In this case, a coordinate system indicating the orientation of the input device gripping portion 200 at the position 400 is set to $\{A\}$, and a coordinate system indicating the orientation of the input device gripping portion 200 at the position 405 is set to $\{B\}$. Further, a coordinate system indicating the orientation of the end effector 142 at the position 410 is set to $\{C\}$, and a coordinate system indicating the orientation of the end effector 142 at the position 415 is set to $\{D\}$.

Since the input device gripping portion 200 is connected by the link or the like, as described in FIG. 3, it is possible to acquire the position $M_p$ and the orientation $M_A R$ of the position 400 in the operation input device absolute coordinate system $\{M\}$ by calculating the kinematics.

In the position and orientation at a time of moving the input device gripping portion 200 to the position 405, the position $M_r$ and the orientation $M_B R$ can be acquired by dissolving the kinematics from the joint value of the link or the like. Accordingly, the change from the position 400 to the position 405 of the input device gripping portion 200 can be written by the following expression (1) by using the homogenous transformation matrix $A_B H$.

$$_B^A H = \begin{bmatrix} _B^A R & (^M r - ^M p) \\ 0 & 1 \end{bmatrix} \quad (1)$$

$$= \begin{bmatrix} _A^M R^{-1} {}_B^M R & (^M r - ^M p) \\ 0 & 1 \end{bmatrix}$$

In the same manner, in the position and orientation of the position 410 of the end effector 142, the position $S_t$ and the orientation $S_C R$ can be acquired as the value in the manipulator absolute coordinate system $\{S\}$ by dissolving the kinetics of the manipulator 134. Expressing as the homogenous transformation matrix $S_C H$, the following expression (2) is written.

$$_C^S H = \begin{bmatrix} _C^S R & ^S t \\ 0 & 1 \end{bmatrix} \quad (2)$$

In the conventional method, the position and orientation $S_D H$ as seen from the manipulator absolute coordinate $\{S\}$ at the target position 415 moving the end effector 142 can be determined by the following expression (3).

$$_D^S H = _C^S H _B^A H \quad (3)$$

$$= \begin{bmatrix} _C^S R & ^S t \\ 0 & 1 \end{bmatrix} \begin{bmatrix} _B^A R & (^M r - ^M p) \\ 0 & 1 \end{bmatrix}$$

$$= \begin{bmatrix} _A^M R _B^M R & ^S t + _C^S R (^M r - ^M p) \\ 0 & 1 \end{bmatrix}$$

However, since this method is based on the fact that the operator comprehends the absolute coordinate system (the horizontal and vertical coordinate system), and the world provided by the three-dimensional stereoscopic vision monitor is recognized definitely, it is hard to operate intuitively.

On the contrary, the present embodiment always employs the method of determining the change of the position and orientation on the basis of the orientation of the input device gripping portion 200. In other words, the moving amount and the changed orientation of the input device gripping portion 200 are calculated by calculating the coordinate system $\{E\}$ set in the input device gripping portion 200 hour by hour, and further correcting the position movement reference data 112 on the basis of the orientation of the input device gripping portion coordinate system $\{E\}$ calculated hour by hour, that is, the elementary vectors Xe, Ye and Ze. The moving amount and the changed orientation of the coordinate system $\{F\}$ of the end effector 142 are calculated by using the moving amount and the changed orientation of the calculated input device gripping portion 200. The position direction of the manipulator 134 is always reflected on the basis of the orientation of the end effector 142, by executing the method by the moving direction compensation controller 116.

Accordingly, on the assumption that the position and orientation in the coordinate {S} of the manipulator 134 using the present embodiment is set to $S_DH'$, since the following expression (4) can be obtained, it is possible to intuitively operate.

$$_D^S H' = \begin{bmatrix} _A^M R_B^M R & ^S t + _C^S R^A q \\ 0 & 1 \end{bmatrix} \quad (4)$$

In this case, for simplification, the coordinate transformations caused by the viewing way of the camera visual field are omitted, however, they may be included. Further, there is a case that a motion scale ratio is set between the motion of the operation input device and the motion of the manipulator. A great motion input by the operation input device may be reflected as a small motion in the manipulator, or the manipulator may be greatly moved with respect to the small operation input inversely, by applying the motion scale ratio to the change amount of the position.

The operator 154 finds a known material or shape on the screen projected on the monitor 152 and defines a world view of the space on the basis of the three-dimensional position and orientation. In the case that the background and the work subject portion projected on the monitor 152 are not known, or constituted by a soft material, the manipulator 134 is actuated on the basis of the orientation of the end effector 142. Accordingly, the method using the present embodiment is extremely effective.

Figure 5A:
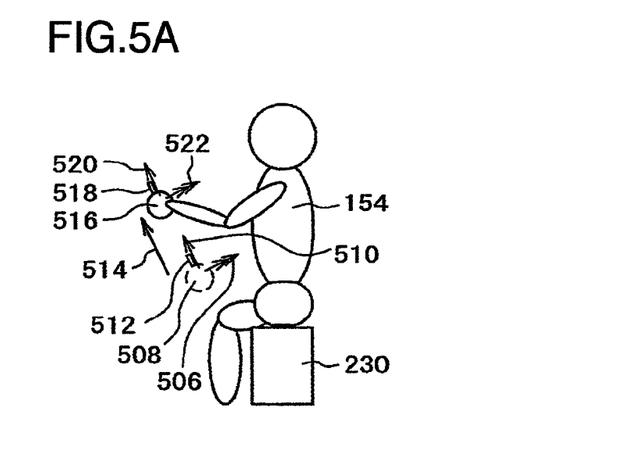
FIGS. 5A to 5E are views explaining an operation example in the present embodiment.
Figure 5B:
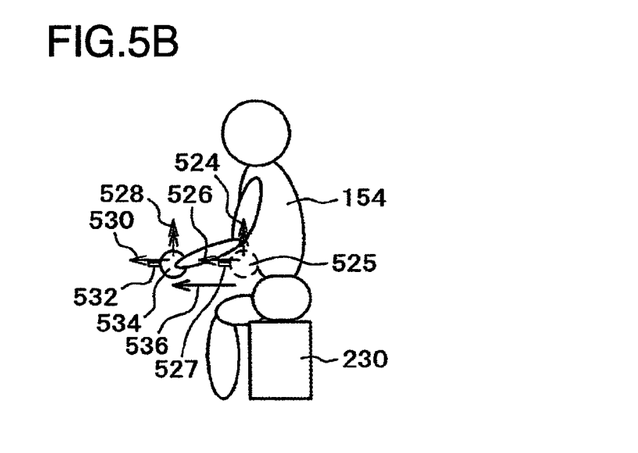
Figure 5C:
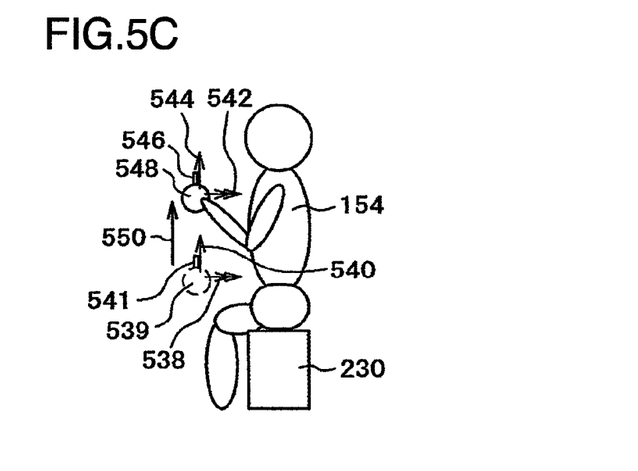
Figure 5D:
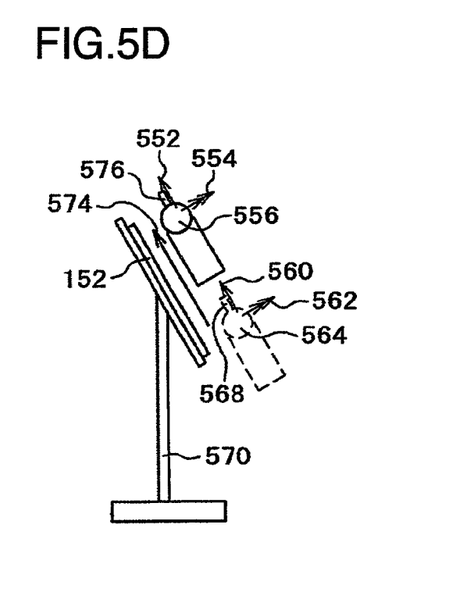
Figure 5E:
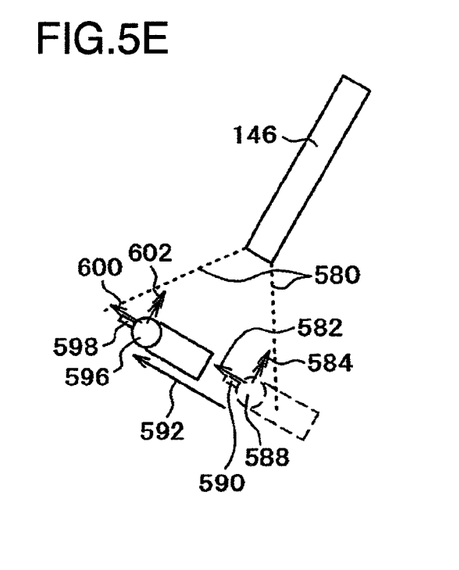

Next, a description will be given of an operation example in the present embodiment with reference to FIG. 5. FIG. 5 is a view explaining the operation example in the present embodiment. FIGS. 5A to 5C show three examples showing a state in which the operator operates the gripping portion interface of the operation input device. FIG. 5D shows the three-dimensional stereoscopic vision monitor referred by the operator, and a state of a motion of the end effector reflected on the monitor by a stereoscopic vision. FIG. 5E shows the end effector and a state of the camera imaging the end effector. In this case, the movement of the end effector on the monitor as shown in FIG. 5D means the movement of the end effector from a position 588 to a position 596. In this case, a dotted line in FIG. 5E shows a camera visual field.

Double arrows 522, 506, 524, 528, 538, 542, 554, 562, 584 and 602 indicate corresponding orientations of the input device gripping portion and the end effector. In the same manner, arrows 520, 510, 526, 530, 540, 544, 560, 552, 582 and 600 indicate corresponding orientations of the input device gripping portion and the end effector. Arrows 514, 536, 550, 574 and 592 indicate moving directions of the input device gripping portion and the end effector.

Grip opening and closing mechanisms 518, 532 and 546 prepared in the input device gripping portions 516, 534 and 548 open and close the end effector, and form markers indicating the orientations of the input device gripping portions 516, 534 and 549.

The operator 154 sits on the chair 230, grips the input device gripping portion 516 connected from a table 570 in which the three-dimensional stereoscopic vision monitor 152 is arranged, by the link or the like (not shown), and executes the operation input for moving the manipulator.

The operator generates a difference of recognition of the three-dimensional space generated by the three-dimensional stereoscopic vision monitor 152, on the basis of an inclination of the three-dimensional stereoscopic vision monitor 152. The operator recognizes the inclination of the three-dimensional stereoscopic vision monitor 152 and the three-dimensional space projected on the monitor being the same as the inclination on the real world. If the operator considers to move the end effector as shown in FIG. 5D, the operator diagonally moves the input device gripping portion 508 such as the arrow 514 in conformity with the inclination of the three-dimensional stereoscopic vision monitor 152 from a state of bringing the orientation of the grip opening and closing mechanism 568 in the three-dimensional stereoscopic vision monitor 152 into line with the orientation of the grip opening and closing mechanism 512, as shown in FIG. 5A, and moves the input device gripping portion and the grip opening and closing mechanism to the positions and orientations 516 and 518.

On the other hand, the operator may consider that a relation between the screen of the three-dimensional stereoscopic vision monitor 152 and the operation input device is vertically shifted like a relation between a monitor and a mouth in a general personal computer. In this case, if the operator considers to move the end effector as shown in FIG. 5D, the operator moves the operation input device as shown in FIG. 5B. In other words, the operator moves horizontally the input device gripping portion 525 such as the arrow 536, from a state in which the orientation of the grip opening and closing mechanism 527 is set horizontal, and moves the input device gripping portion and the grip opening and closing mechanism to the positions and orientations 534 and 532.

Further, the operator 154 may recognize that the three-dimensional stereoscopic vision monitor 152 installed in the inclined manner stands vertically. In this case, if the operator considers to move the manipulator as shown in FIG. 5D, the operator moves the operation input device vertically to the ground surface as shown in FIG. 5C. In this case, the operator moves horizontally the input device gripping portion 539 as shown by the arrow 550 from the state in which the orientation of the grip opening and closing mechanism 541 is set horizontal, and moves the input device gripping portion and the grip opening and closing mechanism to the positions and orientations 548 and 546.

In order to achieve the motion of FIG. 5D in correspondence to the difference of the recognition of the operator as mentioned above, the various operating methods exist such as FIGS. 5A to 5C.

If the present embodiment is applied, the motion shown in FIG. 5D can be achieved whatever moving way in FIGS. 5A to 5C is employed. Any time for being accustomed to the device is not necessary regardless of the difference of the recognition by the operator, it is possible to intuitively operate the manipulator, and the present embodiment is very effective.

In the case that two sides of the end effector are symmetrical, and are seen identical, a difference between two sides can be recognized by attaching a mark on the front side or the back side.

The operator can intuitively operate the manipulator without being sensitive about the position relation between the monitor and the operation input device, the position relation of the camera and the like, by setting the change of the position and orientation input by the operation input device to the position movement command on the basis of the orientation hour by hour.

In accordance with the present embodiment, it is possible to achieve the intuitive master-slave operation without being sensitive about an operation in a state in which the orientations of the operation input device and the actual manipulator are offset, and a displacement of the orientation generated in the case that it is necessary to operate a lot of arms by one operation input device, or without defining the position relation between the operation input device and the monitor, and a necessity of a method of synchronizing the orientation of the gripping portion of the operation input device with the orientation of the end point leading end of the manipulator by the actuator.

In accordance with the present embodiment, the manipulator leading end has six degrees of freedom in the position and orientation, and the manipulator can be operated without being sensitive about the correspondence of the position and orientation between the motion direction of the operation input device and the motion direction of the manipulator at a time of operating the position and orientation by the operation input device. Further, since the system can be constructed by particularly defining the layout relation of the operation input device, the monitor, the camera, the manipulator and the like, the system becomes simple, and is effective. Further, since it is not necessary to incorporate the power source such as the actuator or the like in the operation input device, the device is inexpensive and can achieve a downsizing. Particularly, in the operation backup master-slave manipulator system, the present embodiment is effective. The defined ground surface, the fixed material or the like does not exist within the body cavity, and it is hard to comprehend the three-dimensional position and orientation relation between the affected part and the manipulator leading end operation tool. The operator carries out the operation while viewing the affected part imaged by the stereoscopic endoscope and the end point leading operation tool of the operation backup manipulator. In this case, since the operator operates by moving the operation input device on the basis of the orientation of the end point leading end operation tool of the operation backup manipulator corresponding to only one know material in the reflected materials in the monitor, the method in accordance with the present embodiment is particularly effective.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A master-slave manipulator system comprising:
a manipulator having an end effector;
a camera imaging said manipulator and a working area of said manipulator;
a monitor displaying an image which said camera images so as to provide;
an operation input device outputting a command for operating said manipulator;
a master controller generating and outputting a control reference data on the basis of the command of said operation input device; and
a manipulator controller controlling a position and orientation of said manipulator on the basis of the control reference data output from said master controller,
wherein said master controller comprises:
an information acquisition portion for operation command acquiring an operation reference data on the basis of the command by said operation input device;
an acquirement information division portion dividing said operation reference data into a position movement reference data and an orientation reference data; and
a moving direction compensation controller compensating said position movement reference data on the basis of said orientation reference data so as to output a position moving command compensation information, and
wherein said manipulator controller is structured to control the position and orientation of said manipulator on the basis of said position moving command compensation information and said orientation reference data.

2. A master-slave manipulator system as claimed in claim 1, wherein said end effector is structured to have the position and orientation having six degrees of freedom, said information acquisition portion for operation command is structured such as to acquire an operation reference data having six degrees of freedom on the basis of the command by said operation input device, and said acquirement information division portion is structured to divide said operation reference data into a position movement reference data having three degrees of freedom and an orientation reference data having three degrees of freedom.

3. A master-slave manipulator system as claimed in claim 2, wherein said moving direction compensation controller is structured to calculate the orientation of said end effector hour by hour, and correct said position movement reference data on the basis of the orientation of the end effector calculated hour by hour.

4. A master-slave manipulator system as claimed in claim 2, wherein said operation input device is provided with an input device gripping portion in a leading end portion, and said moving direction compensation controller is structured to calculate the orientation of said input device gripping portion hour by hour, calculate a moving amount and a changed orientation of said operation input device on the basis of the orientation of the input device gripping portion calculated hour by hour, and calculate a coordinate of said end effector hour by hour by using the calculated moving amount and changed orientation of said operation input device.

5. A master-slave manipulator system as claimed in claim 2, wherein said operation input device is provided with a moving mechanism having three direct acting joints and three rotating joints and a sensor such as an encoder, a potentiometer or the like capable of acquiring each of joint values, and said information acquisition portion for operation command is structured such to acquire the operation reference data having six degrees of freedom on the basis of an electric signal of the position and orientation acquired by said sensor.

6. A master-slave manipulator system as claimed in claim 3, wherein said operation input device is provided with a moving mechanism having three direct acting joints and three rotating joints and a sensor such as an encoder, a potentiometer or the like capable of acquiring each of joint values, and said information acquisition portion for operation command is structured to acquire the operation reference data having six degrees of freedom on the basis of an electric signal of the position and orientation acquired by said sensor.

7. A master-slave manipulator system as claimed in claim 4, wherein said operation input device is provided with a moving mechanism having three direct acting joints and three rotating joints and a sensor such as an encoder, a potentiometer or the like capable of acquiring each of joint values, and said information acquisition portion for operation command is structured to acquire the operation reference data having six degrees of freedom on the basis of an electric signal of the position and orientation acquired by said sensor.

8. A master-slave manipulator system as claimed in claim 5, wherein said operation input device is provided with an input device gripping portion for manually operating said moving mechanism in a leading end portion of said moving mechanism, and said information acquisition portion for operation command is structured to acquire the position and orientation of the input device gripping portion on the basis of an electric signal acquired by said sensor.

9. A master-slave manipulator system as claimed in claim 6, wherein said operation input device is provided with an input device gripping portion for manually operating said moving mechanism in a leading end portion of said moving mechanism, and said information acquisition portion for operation command is structured to acquire the position and orientation of the input device gripping portion on the basis of an electric signal acquired by said sensor.

10. A master-slave manipulator system as claimed in claim 7, wherein said operation input device is provided with an input device gripping portion for manually operating said moving mechanism in a leading end portion of said moving mechanism, and said information acquisition portion for operation command is structured such as to acquire the position and orientation of the input device gripping portion on the basis of an electric signal acquired by said sensor.

11. A master-slave manipulator system as claimed in claim 8, wherein a plurality of said manipulators are installed, and said operation input device is constituted by a double arm type operation input device.

12. A master-slave manipulator system as claimed in claim 9, wherein a plurality of said manipulators are installed, and said operation input device is constituted by a double arm type operation input device.

13. A master-slave manipulator system as claimed in claim 10, wherein a plurality of said manipulators are installed, and said operation input device is constituted by a double arm type operation input device.

14. A master-slave manipulator system as claimed in claim 4, wherein said end effector is constituted by an operation tool, said camera is constituted by a three-dimensional endoscope, and said input device gripping portion has a grip opening and closing mechanism for opening and closing said operation tool.

* * * * *